United States Patent [19]

Dechene et al.

[11] Patent Number: 5,162,103
[45] Date of Patent: Nov. 10, 1992

[54] SAMPLE HOLDER COMPACTOR FOR INDUSTRIAL NMR ANALYSIS

[75] Inventors: Ronald L. Dechene, Boxford; Russell S. Girgenti, Hamilton, both of Mass.

[73] Assignee: Auburn International, Inc., Danvers, Mass.

[21] Appl. No.: 822,119

[22] Filed: Jan. 17, 1992

[51] Int. Cl.⁵ .............................. B01L 9/00
[52] U.S. Cl. .................... 422/104; 436/173; 324/300; 100/245
[58] Field of Search ............. 422/58, 99, 104; 73/38; 436/173; 324/300, 307, 310, 303; 425/408, 411; 100/245, 246, 240

[56] References Cited

U.S. PATENT DOCUMENTS

| | | | |
|---|---|---|---|
| 3,929,060 | 12/1975 | Burke | 100/245 |
| 3,966,973 | 6/1976 | Henry et al. | 324/307 |
| 4,715,212 | 12/1987 | Johanson | 73/38 |
| 4,848,222 | 7/1989 | Fleissner | 100/246 |
| 5,024,559 | 6/1991 | Beuchel | 426/408 |

Primary Examiner—James C. Housel
Assistant Examiner—Lien Tran
Attorney, Agent, or Firm—Jerry Cohen; Edwin H. Paul

[57] ABSTRACT

A sample holder and compactor system (10), for use in an industrial NMR (or like) instrument, wherein particulate non-uniform samples can be loaded and compacted. The system comprises a tubular holder/compactor member (20) with an internal sleeve (26) and a ram (30), all fabricated from materials that are non-interactive with the excitation NMR fields and do not interfere with the sample analysis and provides a repeatable, simple way of handling disparate materials in routine repeatable ways ensuring reliable NMR analyses.

7 Claims, 2 Drawing Sheets

SAMPLE HOLDER COMPACTOR FOR INDUSTRIAL NMR ANALYSIS

FIELD OF THE INVENTION

The present invention relates to apparatus for holding and compacting a series of particulate solid samples that are to be processed by nuclear magnetic resonance (NMR) analysis techniques (including pulsed) or other like treatment for testing and/or manufacturing purposes. The holder/compactor uniformly compresses the solid sample into a repeatable, known volume, and the holder/compactor material is non-active and non-responsive to the excitation fields, therefore not interfering with the analysis or other treatment of the sample.

BACKGROUND OF THE INVENTION

NMR techniques have grown extensively over the past forty years, most notably in the medical instrumentation areas where in vivo examination of various parts of the human body may be seen and in clinical research laboratory uses. In addition there has been some application of these techniques to industrial instrumentation and control tasks, notably as described in the prior U.S. Pat. No. 5,015,954 of Dechene et al. issued on 14 May 1991 and U.S. Pat. No. 5,049,819 issued Sep. 17, 1991, of Dechene et al. both assigned to Auburn International Inc.. Danvers Mass., the disclosures of which are incorporated herein by reference as though st out at length herein. The present invention enables the user to efficiently and effectively handle particulate solid samples of non-uniform composition (e.g. raisins, chocolate and nuts in cookies), texture and surface characteristics (e.g. "stickiness", and granularity).

Present techniques for handling non-uniform specimens (samples) call for separation of the various component parts e.g. raisons, nuts, crumbs, chocolate. Each component is placed in a test tube or other such holders with spatulas or whatever utensil seems to work. The analysis is performed on each component part, and the results are combined for reporting purposes. This separation leads to several sources of error including the following: (a) the relative proportions of the components parts are handled separately, (b) the analyses are performed at different times with different operators and instrument settings. To eliminate these errors, it is desirable to analyze the entire non-uniform sample at the same time. However this presents some problems.

For example there is a need to determine (using NMR techniques) the water content of a whole cookie, including the raisins, chocolate, sugar, nuts, crumbs, etc. The components are all different sizes and textures making it difficult to physically put them into the same test tube. Additionally some of the ingredients are sticky (sugar), some will crumble (nuts), some will not crumble (raisins), some will flow easily (crumbs), some will not flow (crushed raisins). Trying to get all the material into a test tube is not easily accomplished, and when the analysis is complete the material is not easily washed out of the test tube.

An object of the present invention is to provide an improved sample-chamber system, with load unload features, for handling particulate non-uniform solid samples for use in NMR instruments and the like.

It is another object of this invention to provide repetitive capture of a uniform, repeatable sample size which leads to accurate, fast determination of the types and quantity of the nuclear species of interest or like parameters.

A further object of this invention is to provide the ability to unload the sample and clean the chamber after analysis in a quick and easy manner.

Another object of this invention is to provide for fabrication of the holder from a material which is magnetically "invisible" (or otherwise invisible to other radiant energy fields that participate in the measuring) and non-active in the frequency and time domains, in relation to the sample, i.e. that will not interfere with the NMR analysis of the sample or modify the response of the sample itself.

Another object of this invention is to accommodate the variations of density, sample type and physical anomalies of diverse samples with an economical holder.

SUMMARY OF THE INVENTION

The present invention meets the foregoing objects through provision of a sample holding and compacting apparatus, with load-unload features, that satisfies the above mentioned objectives, constructed with non-NMR responsive, inert materials.

The apparatus comprises a housing with an internal chamber of elongated form with a movable ram therein and having a port (opening) in the housing through which a sample may be loaded and unloaded. When the port is closed the ram may be manually pushed via an extension from the ram extending out of the housing to compact (compress) the material within the chamber to a given volume. The dimensions and form of the housing, including the chamber, the port and the compression ratio of the ram, may be of any practical size to accommodate the instrument. However, in a preferred embodiment a cylindrical form for the housing and inner chamber is used. The particulate sample, continuing the cookie example, is crumbled (retaining al the component parts) and poured through the port into the chamber. The opening, in a preferred embodiment, is a single lateral port which extends along almost the entire length of the chamber so that substantially the entire chamber is exposed when the port is opened allowing all the larger components to enter (and later exit) the chamber. After loading the port is closed thereby containing the sample within the chamber and the ram is activated to compress the sample to a preselected volume. This volume is of a size which is best suited to the particular NMR (or other) instrument being used. In this way samples of different densities or other characteristics can be compacted as the user may determine is optimum.

In addition, in another preferred embodiment, the holder may be designed and used such that the ram is pushed by a known force. Here the sample will be compacted until a given pressure is formed within the sample.

The housing is made preferably of glass or non-protonic ceramic, however fluorocarbon or reinforced fluorocarbon are acceptable. These fluorocarbon materials are non-responsive to NMR excitation signals, or produce signals which are easily filtered out or otherwise discarded. It is important that the materials of the holder do not generate any signals which may be interpreted as components of the decay or other response signals generated by the sample under test, or otherwise modify the sample response signals in any way.

In a referred embodiment, the housing is constructed and arranged to ease manual handling, a clamp and keying mechanism attached to the housing positions the sample chamber at the proper location within the instrument for excitation by the driving signals and sending of the response signals. The dimensions may vary as the test context dictates.

In a preferred embodiment a sleeve rotates within a tube, both tube and sleeve having opening which align forming a port into the sample chamber through which a sample is loaded and unloaded. The port extends along almost the entire length of the sample chamber allowing access to the entire chamber. The sleeve is then rotated enclosing and containing the sample within the sample chamber. The ram can then be activated compressing the sample by reducing the sample chamber size.

Other objects, features, and advantages will be apparent from the following detailed description of preferred embodiments taken in conjunction with the accompanying drawing in which:

DETAILED DESCRIPTION OF PREFERRED EMBODIMENTS

Figures 1A, 1B:
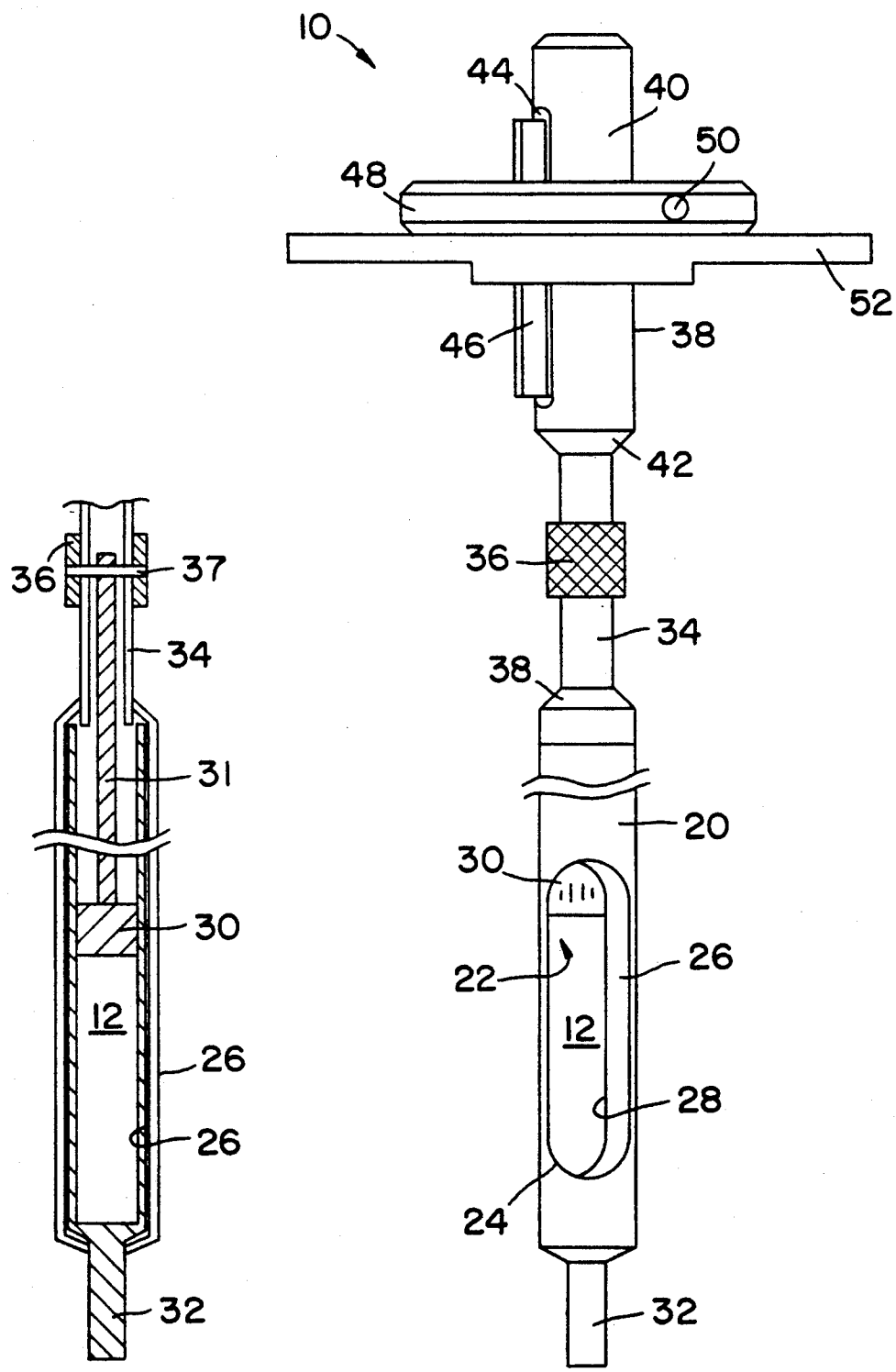
FIG. 1A is a side view of a preferred embodiment of the holder, tube and sleeve openings and the ram.
FIG. 1B is a partial cross section side view of the tube, sleeve, ram and the collar illustrating the interconnections.

FIG. 1A shows the sample holder/compactor system 10 comprising a sample chamber 12 formed in a lower tube 20 that has a diameter, typically, of about ¾ inches and about 0.05 inch wall thickness. This tube has an oval opening 22, typically about three inches long, whose edge 24 is shown, and there is a concentric cylindrical sleeve 26, coaxial with and within the tube, with a wall thickness of about 0.05 inches. The sleeve has an opening, also about three inches long, whose edge 28 is shown nearly aligned with the tube opening edge 24 providing an opening, or port, into the sample chamber 12. A ram 30 is slidably mounted within the sample chamber 12 which is about three inches long with the ram retracted. The port traverses the length of the chamber. The openings in the tube and sleeve extend over about 90° of the circumferences of the tube and sleeve, respectively, fully exposing the sample chamber when such openings are aligned with other.

The sleeve can be rotated, around the common axis shared by the tube and the sleeve by use of a finger tab 32 which is an integral extension of the sleeve through the tube. By manually (or with a motor drive) twisting the tab, the port into the sample chamber may be opened and closed. A sample is loaded into the sample chamber 12 through this port. The sleeve is then rotated to close the port so that the sample is sealed and retained within the chamber. Reverse the rotation to open the sleeve.

Referring to FIG. 1B, the ram 30, a solid cylinder plugging the inner cross-section of the sleeve, is connected to a linear drive shaft 31. A pin 37 attaches the drive shaft to the collar 36. The axial position of the ram is displayed by the position of the collar. The ram-shaft-collar assembly moves longitudinally along the tube, sleeve and ram axis. The travel distance of the assembly is about one inch as determined by the length of the slot in the tube extension 34. Pin 37 physically stops downward movement of the collar at an end level 38 and upward movement of the collar at an end level 42. Typically, the effective sample chamber length is about three inches long with the collar at 42 (ram retracted) and about two inches long when the collar is at 38 (ram extended).

Referring back to FIG. 1A the upper tube 40 has a slot 44, parallel (or approximately so) with the axis. A keying protrusion 46, about six inches long, is mounted in the slot and extends outward beyond and axially along the tube outer surface. The protrusion mid point is about one and one-half feet from the sample chamber mid point. When the sample holder is inserted into an NMR instrument through a washer 52, located below the clamp, with a slotted channel matching the keying protrusion, the rotational position of the tube opening, with respect to the axis and to the NMR, is fixed. A clamp 48, with a matching channel for the protrusion is provided, which may be placed at any position along the protrusion. The clamp 48 may be fixed to the tube, by tightening a screw 50, at a position that defines the distances from the clamp to the sample chamber.

In another preferred embodiment stops (not shown) within the tube extension 34 limit the travel of the ram. Alternatively, when there is a sample in the chamber the user may stop the ram when the sample is compressed enough as determined by the user.

Figure 2B:
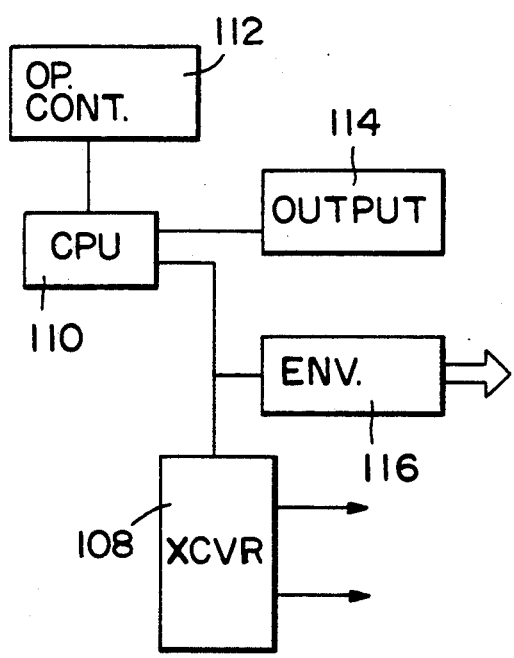
FIG. 2A is a longitudinal section view of the holder inserted into an NMR instrument, showing the relationship of the holders components and the sample chamber to the NMR coils and FIG. 2B indicates other components of the instrument in block diagram form.
Figure 2A:
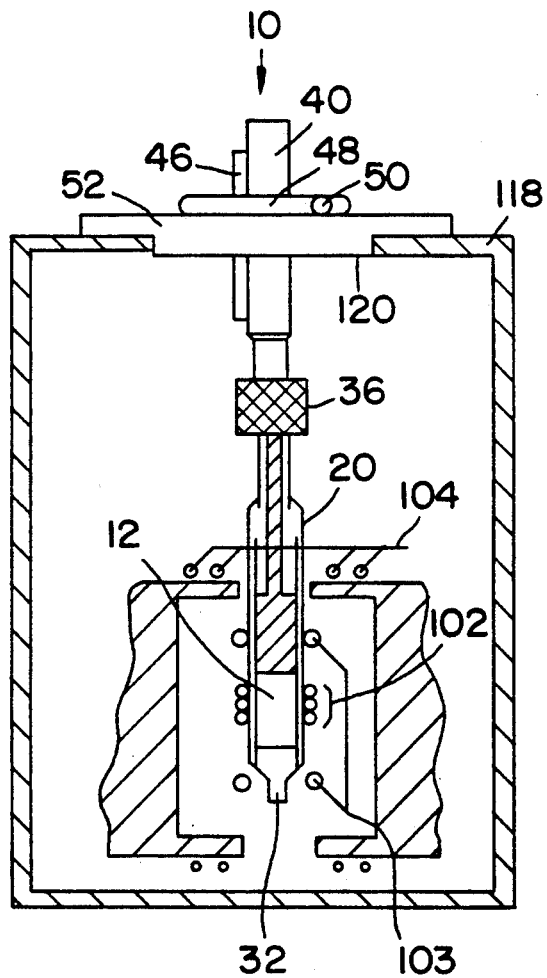

FIG. 2 shows the sample holder/compactor system loaded, sealed and inserted through an opening 120 in an NMR instrument 100 which comprises a transmit-receive RF (radio frequency) coil 102; opposed field coils 104; a transceiver (XCVR) 108; a central processing unit (CPU) 110; operator controls 112; system output 114 such as a recorder, process controller, display device, etc.; an environmental control (ENV) 116, and a measuring region housing 118 with the opening 120. The clamp 48, fixed to the cylinder 40 by the screw 50, seats on the fitted washer 52 and spacer and is attached to the top end fitting positioned in the opening 120 at the top of the instrument's measuring region housing 118. The distance from the bottom of the clamp to the measurement area in the sample chamber may vary between 12 to 18 inches or more (determined by tightening the clamp with the screw at the correct height). This positions the sample chamber 12 in the center of the antenna coils 102. Within the housing there are various shields (not shown) to prevent outside fields from entering the sample region, and to tailor the static field in the sample region to desired strength, uniformity, etc. Additionally active shielding Faraday coils 103 at the ends of the antenna coils limits and shapes the fields in the sample chamber.

The overall dimensions of the apparatus can be any value which accommodates the NMR instrument (or other instruments) and the sample. Although there are practical limits this apparatus can be orders of magnitude larger of smaller, allowing samples ranging from micro-grams to pounds.

Sample tube compositions can distort NMR readings if the materials respond in domains similar to the protons of interest in the sample. If glass is not used (and it is preferred to avoid glass in industrial usage), then the replacement should not be a hydrocarbon plastic. Fluorocarbons can be effective in several applications since signals from fluorine act out of resonance (with conditions tuned to resonance or slightly off resonance as stated hereinabove for hydrogen in moisture measurements) and can be distinguished from moisture related readings at the levels of sensitivity required for such readings and if desired can be filtered (or distinguished). In other cases of higher sensitivity measurements, e.g., for gauging relative proportions of amorphous and crystalline species in mixtures thereof, the sample container should be glass or non-protonic ceramic. In some instances, however, fluorocarbon or reinforced fluorocarbon can be used acceptable for plastic samples. In all such cases the point is to avoid sample containers made from materials with species that can couple with transmitted energy and generate a FID decay curve mimicking the samples.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. An industrial nuclear magnetic resonance or NMR instrument in combination with a sample holder for particulate solid samples said sample holder comprising:
   (a) a sample holding chamber in a housing having one or more opening means therethrough by which samples may be loaded and unloaded,
   (b) means for closing said opening means,
   (c) means for compacting a sample within the chamber, and
   (d) means for positioning and securing said sample holder in a housing of the NMR instrument.

2. A sample holder system as defined in claim 1, wherein said housing is fabricated from materials which do not react to NMR excitation signals.

3. A sample holder system as defined in claim 1 wherein said sample chamber comprises an elongated dead-ended tubular sleeve internally coaxially mounted in a tube, said sleeve provided with an elongated lateral opening for loading and unloading a sample therethrough, the dead end defining a first end of the sample chamber, said compacting means comprises a movable tubular ram, coaxial with and positioned within said sleeve wherein said sleeve and ram are constructed and arranged with an axial sliding fit over a tubular circumference of said ram, said ram defining an axial variable second end of said sample chamber and further comprising means for moving said ram longitudinally within the sleeve and for relatively rotating the sleeve within the tube, the tube having a lateral opening which is alignable with the sleeve's lateral opening through such rotation.

4. A sample holder system as defined in claim 4 further comprising a keying means for fixing the rotational position of said tube lateral opening relative to the instrument.

5. A sample holder system as defined in claim 5 wherein said keying means comprises a lateral protrusion extending outward from the outer surface of the tube.

6. A sample holder system as defined in claim 5 further comprising clamping means, wherein said clamping means is arranged and constructed to be adjustably disposed at any of a plurality of positions along said tube for adjusting the position of said sample holder within the instrument.

7. An industrial NMR sample holder for particulate solid samples comprising:
   a tube with an opening for loading samples,
   a tubular sleeve, with an opening for loading samples, coaxial with said tube, positioned within said tube, the tube and sleeve arranged and constructed with a close sliding fit generally over an outer surface of the sleeve and an inner surface of the tube, wherein the inside of said sleeve forms a sample holding chamber with a first closed end said sleeve being rotatable relative to said tube on a common axis thereof wherein said sleeve can be rotated such that said chamber is closed within said tube and sleeve, and wherein said sleeve and tube are arranged and constructed such that the sleeve can be rotated so that the openings in both the tube and the sleeve are overlapping allowing sample to be loaded and unloaded,
   a ram coaxial with and within said sleeve, arranged and constructed to move along the common axis, forming a second end of said sample chamber, said sleeve and ram are constructed and arranged with a close sliding fit over a tubular circumference of said ram, said sample chamber is defined by said sleeve, said first end and said ram,
   means for moving said ram longitudinally along said axis to reduce the sample volume in said chamber by compressing said sample therein or to enlarge the sample volume in said chamber in order to remove said sample,
   a keying protrusion extending radially from said tube and extending longitudinally along an outer surface of said tube, wherein a rotational position of tube opening can be fixed with respect to said instrument, and
   clamping means for positioning the holder within the instrument, said clamping means extending radially from and circumferentially about said tube outer surface, wherein said clamping means is axially movable over a plurality of positions, each position defining an axial distance from the sample chamber to the clamping means, and wherein the clamping means may be fixed to the tube at each position, and
   a housing constructed of materials that are electrically non-interactive with said NMR instrument and so produce no output signals which can interfere with the NMR sample analysis.

* * * * *

UNITED STATES PATENT AND TRADEMARK OFFICE
CERTIFICATE OF CORRECTION

PATENT NO. : 5,162,103
DATED : November 10, 1992
INVENTOR(S) : Ronald L. Dechene, Russell S. Girgenti It is certified that error appears in the above-identified patent and that said Letters Patent is hereby corrected as shown below:

Column 1, line 30 change "st" to -- set --

Column 2, line 39, change "al" to -- all --

Column 4, line 33, change "2" to -- 2A --

Column 4, line 35, delete [100]

Signed and Sealed this

Tenth Day of January, 1995

Attest:

BRUCE LEHMAN

Attesting Officer    Commissioner of Patents and Trademarks